US006225514B1

(12) United States Patent
Cook et al.

(10) Patent No.: US 6,225,514 B1
(45) Date of Patent: May 1, 2001

(54) RING HALOGENATION OF AROMATIC COMPOUNDS

(75) Inventors: Charles M. Cook, Williamsville; Michael C. Hausladen, Amherst; Michael C. Savidakis, Niagara Falls; Michael J. Fifolt, Grand Island, all of NY (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

(21) Appl. No.: 09/547,385

(22) Filed: Apr. 11, 2000

Related U.S. Application Data

(62) Division of application No. 09/156,861, filed on Sep. 18, 1998, now Pat. No. 6,124,512.
(51) Int. Cl.[7] .............................. C07C 17/00; C09K 3/00
(52) U.S. Cl. ................ 570/208; 252/183.11; 252/183.13
(58) Field of Search ......................... 252/183.11, 183.13; 570/208

(56) References Cited

U.S. PATENT DOCUMENTS 4,236,033 * 11/1980 Aifs .
5,126,489 * 6/1992 Kurek .
5,191,139 * 3/1993 Sanderson .

* cited by examiner

*Primary Examiner*—Paul J. Killos
(74) *Attorney, Agent, or Firm*—Richard D. Fuerle; Anne E. Brookes

(57) ABSTRACT

Disclosed is a method of halogenating the ring of an aromatic compound. The aromatic compound is contacted with a halogenating agent in the presence of a heterogeneous catalyst. The catalyst is the calcination reaction product of:

(A) 51 to 99 wt % of a support which comprises at least one inorganic oxide or hydroxide of at least one metal that is at least divalent and forms a metal-to-oxygen matrix during calcination; and (B) 1 to 49 wt % of at least one dopant which comprises a compound that places an element that is at least divalent, bonded to oxygen atoms, into said matrix during said calcination, resulting in the formation of an acidic solid.

20 Claims, No Drawings

RING HALOGENATION OF AROMATIC COMPOUNDS

This application is a division of application Ser. No. 09/156,861, filed Sep. 18, 1998, U.S. Pat. No. 6,124,512.

BACKGROUND OF THE INVENTION

This invention relates to the halogenation of the ring of an aromatic compound. In particular, it relates to that halogenation using a heterogeneous catalyst that is the reaction product of a support and a dopant.

Chlorinated aromatic compounds are important intermediates for making pharmaceuticals, herbicides, fungicides, and other chemicals. The chlorination of an aromatic ring requires the presence of a catalyst. Both homogeneous (single phase) catalysts, such as various metal chlorides (e.g., aluminum trichloride) and heterogenous (more than one phase) catalysts (e.g., silica, alumina, and various zeolites) have been used for this purpose. While these catalysts are effective, they are not easy to use. Homogeneous catalysts have to be kept anhydrous, more than one equivalent of the catalyst is needed for substrates that contain Lewis base sites, and it is sometimes difficult to separate the product from the catalyst. Heterogeneous catalysts, on the other hand, tend to decompose under the reaction conditions.

SUMMARY OF THE INVENTION

We have discovered that certain non-zeolytic heterogeneous catalysts are very effective in reactions in which an aromatic ring is halogenated. Because these catalysts are solids, separation of the liquid product can be easily accomplished by filtration or decantation and water extraction or distillation is not needed to remove the catalyst. Unlike some previous catalysts used for this reaction, the catalysts of this invention do not readily decompose in the presence of corrosive acids. The catalysts are applicable to the halogenation of many different types of aromatic ring compounds. Using these catalysts, one or more halogens can be added to an aromatic ring.

DESCRIPTION OF THE PREFERRED EMBODIMENTS

Virtually any kind of aromatic compound having sites available on an aromatic ring (i.e., hydrogen atoms) can be halogenated according to the process of this invention. While benzene and benzene derivatives are preferred as they are commercially more important, naphthalene, anthracene, and other multiple aromatic ring structures can also be used as the substrate. Aromatic rings that are substituted with nitrile, alkyl, halogen, acid chloride, carboxylic acid, hydride, and other groups can also be halogenated according to the process of this invention. Examples of single ring aromatic compounds that can be halogenated in the process of this invention include benzene, chlorobenzene, chlorotoluene, p-chlorobenzotrifluoride, 3,4-dichlorobenzotrifluoride, p-methylbenzoylchloride, methyl p-methylbenzoate (a.k.a. methyl p-toluate (MPT)), toluene, methyl 2-chloro p-toluate, methyl 4-chloromethylbenzoate, o-xylene, m-xylene, p-xylene, benzotrifluoride, m-trifluoromethyl benzotrifluoride, p-chlorobenzonitrile, and alkyl and dialkyl benzenes. The preferred class of substrates has aromatic rings that are deactivated towards electrophilic aromatic substitution, such as benzoates, nitrites, benzotrihalides, and halogenated aromatics.

Any halogenating agent can be used, but chlorinating and brominating agents are preferred as those products are more important commercially. Examples of halogenating agents include $F_2$, $SF_4$, $XeF_2$, $I_2$, ICl, $ICl_3$ IBr, $Br_2$, BrCl, $SO_2Cl_2$, $Cl_2$, $SOCl_2$, $COCl_2$, $C_2O_2Cl_4$, $C_3O_3Cl_6$, and n-chlorosuccinimide. Chlorine and bromine are preferred as they are inexpensive and readily available. The amount of halogenating agent used should be stoichiometric with the desired product. That is, a 1 to 1 molar ratio of the halogenating agent to the substrate will add 1 halogen while a 2 to 1 molar ratio of the halogenating agent to the substrate will add 2 halogens, etc. The positions to which the halogens are added proceed in the order of the normal rules of halogen addition.

The catalysts of this invention, commonly known as "solid acid catalysts," can be made by reacting a dopant with a support. The support is at least one inorganic oxide of at least one metal that is at least divalent and which forms a metal-to-oxygen matrix on calcination, such as

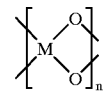

Supports that can be used include $TiO_2$, $ZrO_2$, $HfO_2$, $MnO_2$, $Fe_2O_3$, $Fe_3O_4$, $GeO_2$, $SnO_2$, $TlO_3$, $Nb_2O_5$, $Ta_2O_5$, $SC_2O_3$, $La_2O_3$, $SiO_2$, and mixtures thereof. The preferred supports are $MnO_2$, $TiO_2$, $ZrO_2$, $Fe_2O_3$, $Fe_3O_4$, and mixtures thereof as they have been found to work well. The support is 51 to 99 wt % of the catalyst weight, and preferably is 80 to 96 wt % of the catalyst weight.

The dopant is a compound that can place oxy anions into the support matrix during calcination. The oxy anions comprise an element that is at least divalent bonded to at least two oxygen atoms. Examples of suitable dopants include $H_2SO_4$, $(NH_4)_2SO_4$, $(NH_4)HSO_4$, $SO_3$, $WO_3$, $H_2WO_4$, $H_2MoO_4$, $(NH_4)_2WO_4$, $(NH_4)_2MoO_4$, $Mo(NO_3)_6$, $W(NO_3)_6$, $MoO_3$, $H_3PO_4$, $(NH_4)_3PO_4$, $(NH_4)_2HPO_4$, $(NH_4)H_2PO_4$, $Cr_2O_3$, and mixtures thereof. The preferred dopants are $WO_3$, $H_2SO_4$, $(NH_4)_2SO_4$, $Cr_2O_3$, and mixtures thereof as they have been found to work well. The oxy anions are 1 to 49 wt % of the catalyst weight and are preferably 4 to 20 wt % of the catalyst weight. For example, about 10 to about 15 wt % $H_2WO_4$ or about 5 to about 10 wt % $H_2SO_4$ is preferably present in the catalyst when the support is zirconia.

Preparation and use of these catalysts for other purposes are known. See, for example, the following literature, herein incorporated by reference: Xuemin Song et al., "Sulfated Zirconia Based Strong Acid Catalyst: Recent Progress," Catal. Rev. Sci. Eng. 38, 329–412 (1996); K. Tanabe et al., "Design of Sulfur Promoted Solid Superacid Catalyst," Successful Design of Catalysts, 99–110, Elsevier Science Publications, T. Inui, editor, 1988; Kazushi Arata, "Solid Superacids," Advances in Catalysis, 37 (1990), 165–211, especially pages 177–204; Tsutomu Yamaguchi, "Recent Progress in Solid Superacids," Applied Catalysis, 61 (1990), 1–25, especially pages 12–23; and M. Misono et al., "Solid Superacid Catalysts," Chemtech, November 1993, 23–29, especially pages 24–25. Many of the catalysts of this invention are commercially available and have been used for the acylation of aromatics with acids and acid halides (e.g., U.S. Pat. No. 5,126,489; M. Hino et al., "Acylation of Toluene with Acetic and Benzoic Acids catalyzed by a solid superacid in a Heterogeneous System" J. Chem. Soc. Chem. Comm. 1985,112–113; and K. Arata et al., "Benzoylation of Toluene With Benzoyl Chloride and Benzoic Anhydride Catalyzed by Solid Superacids on Sulfate Supported Alumina," Applied Catalysis, 59 (1990) 197–204). They have also been used for the oligomerization of olefins (e.g., U.S. Pat. Nos. 5,191,139; 5,113,034; and 5,304,696), the alkylation of phenol (e.g., U.S. Pat. Nos. 4,236,033 and 5,304,688), and the akylation of aromatics with olefins (e.g., U. S. Pat. Nos. 5,243,115; 5,396,011; 5,516,954; and 5,563, 311). The catalysts have been used for reactions which traditionally use Bronstead acid-Lewis acid combinations as catalysts, such as carbonylation of aromatics with carbon monoxide to form aromatic aldehydes (U.S. Pat. No. 5,679, 867; T. H. Clingenpeel et al., "$C^{13}$ Study of the Carbonylation of Benzene with CO on Sulfated Zirconia," J. Am. Chem. Soc. (1997), 119(23), 5469–5470) and the alkylation of aromatics with benzyl chlorides (K. Tanabe et al., "Benzylation of Toluene with Benzyl Chloride," Proceedings of the $8^{th}$ International Congress on Catalysis, Vol. 5, Verlag Chemie, Berlin (1984), pg 601; S. N. Koyande et al., "Reaction Kinetics of Benzene With Benzyl Chloride on Sulfate-Treated Metal Oxide Catalysts," Ind. Eng.Chem. Res. (1998), 37, 908–913). Zirconium containing pentasil ad. (acidic) zeolites, where part of the alumina in the aluminosilicate matrix has been replaced with zirconia, have been used to isomerize chlorinated aromatics (e.g., U.S. Pat. No. 4,935,561) and have increased lifetime as compared to the non-zirconia containing pentasil zeolites.

The catalysts can be made by contacting the amorphous support with a solution of a soluble salt of a dopant, drying, and repeating this procedure until the desired amount of dopant has been absorbed onto the support. Alternatively, the dopant can be precipitated onto the support or dry dopant and support can be mixed. Then the doped support is calcined in air, typically at about 450 to about 850° C. for up to 5 hours or more, the time and temperature of calcination depending upon the particular catalyst. Calcining for too long or at too high a temperature can deactivate the catalyst. During calcining, the dopant reacts with a support to form various complicated oxygen-bridged matrices.

The resulting catalyst is a solid that resists halogen attack and hydrogen halide attack, has enhanced acidity, and is insoluble in the reaction medium. It preferably has a Hammett Acid Strength (—HO) of at least 11.9 (i.e., at least as acidic as sulfuric acid). For a more detailed description of the catalysts used in this invention see, for example, the article, "Solid Superacids," by K. Tanabe et al. in *Heterogeneous Catalysis*, G. Ertl et al. (Wiley VCH, 1997), and U.S. Pat. Nos. 4,918,041; 4,956,518; 5,019,671; 5,310,868; 5,321,197; 5,345,028; 5,396,011; and 5,516,954. Generally, catalysts that work in isomerization reactions will work in the halogenation reactions of this invention, provided they are resistant to both the halogen and its hydrogen halide. The catalyst should be stable under the reaction conditions. Fluorination, for example, should be performed with catalysts that do not dissolve in the fluorinating agent, such as zirconia-based catalysts.

The halogenation can be performed with or without a solvent, but it is preferably performed neat as that results in a higher throughput for a given amount of equipment. However, if the substrate or the product is a solid above the desired reaction temperature, it is preferable to use enough solvent to dissolve the substrate. Examples of solvents that can be used include methylene chloride, ethylene dichloride (EDC), carbon tetrachloride, chloroform, 1,1,1-trichloroethane, hydrofluoroethers, perfluoroethers, and various fluorocarbons sold under the trademark, "Freon." Ethylene dichloride is preferred due to its higher boiling point.

The halogenation reaction can be performed continuously or in a batch process. About 0.1 to about 50 wt % catalyst, and preferably about 1 to about 20 wt % catalyst, based on substrate weight, can be used for a batch reaction. Less catalyst requires a longer reaction time and more catalyst is unnecessary and of no additional benefit. However, more or less catalyst can be present if the reaction is continuous, depending on whether the wt % of catalyst is calculated based on the amount of substrate being processed at a given time or on the total substrate processed before the catalyst is exhausted, respectively.

The reaction will occur between −25 and 300° C. Lower temperatures require a longer time and higher temperatures may result in unwanted byproducts. The preferred temperature range is about 20 to about 100° C. Performing the reaction under pressure increases the reaction rate, but pressures over about 600 psi require special equipment. If the halogenating agent is chlorine gas at high temperatures, higher pressures may be needed to dissolve it. A preferred pressure range is about 0 to about 100 psi. The reaction time will depend upon the particular substrate being halogenated, the catalyst being used, and the reaction conditions. The reaction can be monitored by halogenating agent consumption, infrared spectroscopy, gas chromatography (GC), specific gravity, off gas, and other means. Since the catalyst is a solid and the product is a liquid, the product can be easily separated from the catalyst by filtration or decantation. It may be possible to regenerate exhausted catalyst by solvent washing or by calcining in oxygen. The product mixture is believed to be novel, except when the aromatic compound is a benzophenone.

The following examples further illustrate this invention.

EXAMPLE 1

Comparative

To a stirred solution of 15.0 g (0.10 mol) of methyl p-toluate (MPT) and 1.62 g (0.01 mol) of $FeCl_3$ in 20 mL of $CH_2Cl_2$ at room temperature was added $Cl_2$. The chlorine addition was carried out over a period of 13.5 hr. A sample of the reaction mixture was analyzed by GC and it was found to contain 92 wt % methyl 3-chloro-p-toluate (3-CMT) and 6 wt % unreacted MPT.

EXAMPLE 2

A mixture of 22.8 g of benzene (0.3 moles), 27.5 g of iodine monochloride (0.169 moles), and 2.0 g of tungstated zirconia calcined at 800° C. for 3 hours was stirred for 20 minutes at 20° C. A copious quantity of HCl off-gassed from the reaction mixture. A GC of the reaction mixture indicated 41% conversion of benzene to a 1.3:1 mixture of chlorobenzene and iodobenzene.

EXAMPLE 3

A. A sample of MPT (26.7 g; 0.178 mol) was chlorinated using 1.94 g (7.3 wt %) of sulfate doped zirconia as a catalyst at 54–68° C. and $Cl_2$ over a period of 140 min. This reaction was carried out in a glass autoclave and no attempts to exclude light were made.

B. Using the same reactor, a sample of MPT (25.6 g; 0.170 mol) was chlorinated using 2.11 g (8.2 wt %) of sulfate doped zirconia as a catalyst and $Cl_2$ at 61–65° C. and 14–15 psig over a period of 110 min. In this case light was excluded from the system by wrapping the reactor with foil.

C. Another chlorination was carried out in the absence of light using a larger reactor. In this case MPT (49.9 g; 0.332 mol) was dissolved in 667 g of 1,2-dichloroethane and chlorinated using 4.93 g (9.9 wt %) of tungsten doped zirconia and $Cl_2$ at 74–86° C. and 46–50 psig over a period of 260 min. Samples of the reaction products were analyzed by GC.

The following table gives the results:

| | | | | | Reaction Conditions | | | | | | | |
|---|---|---|---|---|---|---|---|---|---|---|---|---|
| | | Calcination | Catalyst | | Time | Temp | Pressure | | | Products | | |
| Ex. | Catalyst | Conditions | (% wt) | Solvent | (min) | (° C.) | (psig) | MPT | Conversion | 3-CMT | CMPT | MCMB | Other |
| A | $SO_4/ZrO_2$ | 600° C./80 min | 7.3 | none | 140 | 58 | 0.0 | 85.9 | 14.1 | 51.1 | 3.5 | 45.4 | 0.0 |
| B | $SO_4/ZrO_2$ | 700° C./150 min | 8.2 | none | 110 | 51–65 | 14–15 | 85.4 | 14.6 | 94.5 | trace | 5.5 | 0.0 |
| C | $WO_3/ZrO_2$ | 700° C./150 min | 9.9 | EDC | 20 | 74 | 46.0 | 92.4 | 7.6 | 76.4 | 0.0 | 23.6 | 0.0 |
| C | $WO_3/ZrO_2$ | 700° C./150 min | 9.9 | EDC | 40 | 77 | 50.0 | 74.9 | 25.1 | 85.2 | 1.3 | 12.4 | 1.1 |
| C | $WO_3/ZrO_2$ | 700° C./150 min | 9.9 | EDC | 60 | 77 | 49.5 | 45.0 | 55.0 | 88.5 | 0.9 | 8.9 | 1.7 |
| C | $WO_3/ZrO_2$ | 700° C./150 min | 9.9 | EDC | 115 | 77 | 49.5 | 27.3 | 72.7 | 89.8 | 0.6 | 7.1 | 2.4 |
| C | $WO_3/ZrO_2$ | 700° C./150 min | 9.9 | EDC | 145 | 77 | 50.0 | 20.7 | 79.3 | 90.2 | 0.6 | 6.6 | 2.7 |
| C | $WO_3/ZrO_2$ | 700° C./150 min | 9.9 | EDC | 175 | 77 | 48.0 | 9.0 | 91.0 | 89.5 | 0.5 | 5.8 | 4.2 |
| C | $WO_3/ZrO_2$ | 700° C./150 min | 9.9 | EDC | 200 | 77 | 48.0 | 4.6 | 95.4 | 88.5 | 0.4 | 5.5 | 5.6 |
| C | $WO_3/ZrO_2$ | 700° C./150 min | 9.9 | EDC | 260 | 86 | 47.0 | 1.2 | 98.8 | 84.5 | 0.2 | 5.1 | 10.1 |

In the above table MPT is the substrate, methyl p-toluate, 3-CMT is the desired product, methyl-3-chloro-p-toluate, CMPT is chloromethyl p-toluate, and MCMB is methyl 4-chloromethylbenzoate. The above experiments show that the catalysts were very effective in producing 3-CMT with very little undesirable byproduct.

We claim:
1. A composition comprising
   (A) an aromatic compound that is not a benzophenone, having at least one aromatic ring with at least one hydrogen atom on said aromatic ring;
   (B) at least one equivalent of a halogenating agent; and
   (C) about 0.1 to about 50 wt % of an acidic solid catalyst that resists attack by said halogenating agent and by its hydrogen halide and is the calcination reaction product of
      (1) 51 to 99 wt % of a support which comprises at least one inorganic oxide or hydroxide of at least one metal that is at least divalent and forms a metal-to-oxygen matrix during said calcination; and
      (2) 1 to 49 wt % of at least one dopant which comprises a compound that places an element that is at least divalent, bonded to oxygen atoms, into said matrix during said calcination.
2. A composition according to claim 1 wherein said aromatic compound has a single aromatic ring.
3. A composition according to claim 2 wherein said aromatic compound is a benzoate, a benzonitrile, a benzotrihalide, or a halogenated benzene.
4. A composition according to claim 1 wherein said aromatic compound is benzene, chlorobenzene, chlorotoluene, p-chlorobenzotrifluoride, 3,4-dichlorobenzotrifluoride, p-methylbenzoyl chloride, methyl p-methylbenzoate, toluene, methyl 3-chloro-p-toluate, chloromethyl p-toluate, methyl 4-chloromethylbenzoate, o-xylene, m-xylene, p-xylene, benzotrifluoride, m-trifluoromethyl benzotrifluoride, p-chlorobenzonitrile, or an alkyl ordialkyl benzene.
5. A composition according to claim 1 wherein said support is $TiO_2$, $ZrO_2$, $HfO_2$, $MnO_2$, $Fe_2O_3$, $Fe_3O_4$, $GeO_2$, $SnO_2$, $TlO_3$, $Nb_2O_5$, $Ta_2O_5$, $Sc_2O_3$, $La_2O_3$, $SiO_2$, or a mixture thereof.
6. A composition according to claim 5 wherein said support is $TiO_2$, $ZrO_2$, $MnO_2$, $Fe_2O_3$, $Fe_3O_4$, or a mixture thereof.
7. A composition according to claim 1 wherein said dopant is $H_2SO_4$, $(NH_4)_2SO_4$, $(NH_4)HSO_4$, $SO_3$, $WO_3$, $H_2WO_4$, $H_2MoO_4$, $(NH_4)_2WO_4$, $(NH_4)_2MoO_4$, $Mo(NO_3)_6$, $W(NO_3)_6$, $MoO_3$, $H_3PO_4$, $(NH_4)_3PO_4$, $(NH_4)_2HPO_4$, $(NH_4)H_2PO_4$, $Cr_2O_3$, or a mixture thereof.
8. A composition according to claim 7 wherein said dopant is $H_2WO_4$, $H_2SO_4$, $(NH_4)_2SO_4$, $CrO_3$, or a mixture thereof.
9. A composition according to claim 1 wherein said halogenating agent is $F_2$, $SF_4$, $XeF_2$, $I_2$, ICl, $ICl_3$ IBr, $Br_2$, BrCl, $SO_2Cl_2$, $Cl_2$, $SOCl_2$, $COCl_2$, $C_2O_2Cl_4$, $C_3O_3Cl_6$, n-chlorosuccinimide, or a mixture thereof.
10. A composition according to claim 1 where said halogenating agent is a chlorinating agent.
11. A composition according to claim 10 wherein said chlorinating agent is chlorine gas.
12. A composition according to claim 1 wherein no solvent is present in said composition.
13. A composition according to claim 1 wherein said aromatic compound is a solid above the temperature at which it halogenates, and is dissolved in a solvent.
14. A composition according to claim 13 wherein said solvent is ethylene dichloride.
15. A composition according to claim 1 wherein the equivalent ratio of said halogenating agent to said aromatic compound is 1:1.
16. A composition comprising
   (A) a substrate of benzoate, a benzonitrile, a benzotrihalide, or a halogenated benzene;
   (B) about one equivalent of chlorine gas;
   (C) about 1 to about 20 wt % of a catalyst made by calcining a support of $TiO_2$, $ZrO_2$, $MnO_2$, $Fe_2O_3$, $Fe_3O_4$, or a mixture thereof with a dopant of $H_2WO_4$, $H_2SO_4$, $(NH_4)_2SO_4$, $CrO_3$, or a mixture thereof, whereby the weight added to said catalyst by said dopant is about 4 to about 20 wt % of said catalyst weight.
17. A composition according to claim 16 wherein said calcining is at about 450 to about 850° C.
18. A composition according to claim 16 wherein said support is zirconia and the weight added to said catalyst by said dopant is about 10 to about 15 wt % $H_2WO_4$ or about 5 to about 10wt % $H_2SO_4$.
19. A composition according to claim 16 wherein said compound is benzene, chlorobenzene, chlorotoluene, p-chlorobenzotrifluoride, 3,4-dichlorobenzotrifluoride, p-methyl benzoylchloride, methyl p-methylbenzoate, toluene, methyl 3-chloro-p-toluate, chloromethyl p-toluate, methyl 4-chloromethyl benzoate, o-xylene, m-xylene, p-xylene, benzotrifluoride, m-trifluoromethyl benzotrifluoride, p-chloro benzonitrile, or an alkyl or dialkyl benzene.

20. A composition comprising
   (A) benzoate, a benzonitrile, a benzotrihalide, or a halogenated benzene;
   (B) about one equivalent of chlorine gas; and
   (C) about 1 to about 20 wt % of a catalyst made by calcining a support of zirconia with a dopant of about 10 to about 15 wt % $H_2WO_4$ or about 5 to about 10 wt % $H_2SO_4$.

* * * * *